United States Patent
Reutter-Maier et al.

(10) Patent No.: US 8,802,399 B2
(45) Date of Patent: Aug. 12, 2014

(54) METHOD FOR PRODUCTION OF NATURAL L-CYSTEINE BY FERMENTATION

(75) Inventors: Anneliese Reutter-Maier, Kirchseeon (DE); Markus Brunner, Munich (DE); Tobias Dassler, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/127,365

(22) PCT Filed: Jun. 25, 2012

(86) PCT No.: PCT/EP2012/062236
§ 371 (c)(1),
(2), (4) Date: Dec. 18, 2013

(87) PCT Pub. No.: WO2013/000864
PCT Pub. Date: Jan. 3, 2013

(65) Prior Publication Data
US 2014/0141474 A1    May 22, 2014

(30) Foreign Application Priority Data
Jun. 30, 2011   (DE) .......................... 10 2011 078 481

(51) Int. Cl.
*C12P 13/12*   (2006.01)
*C12P 17/14*   (2006.01)

(52) U.S. Cl.
CPC *C12P 13/12* (2013.01); *C12P 17/14* (2013.01)
USPC .................... 435/113; 435/69.1; 435/252.31; 536/23.1

(58) Field of Classification Search
None
See application file for complete search history.

(56) References Cited

U.S. PATENT DOCUMENTS

| | | |
|---|---|---|
| 5,972,663 A | 10/1999 | Winterhalter et al. |
| 6,218,168 B1 | 4/2001 | Leinfelder et al. |
| 7,582,460 B2 | 9/2009 | Maier et al. |
| 2003/0077766 A1 | 4/2003 | Takagi et al. |
| 2004/0038352 A1 | 2/2004 | Maier |
| 2005/0221453 A1 | 10/2005 | Takagi et al. |
| 2008/0190854 A1 | 8/2008 | Boehm |
| 2009/0053778 A1 | 2/2009 | Sauer et al. |
| 2010/0093045 A1 | 4/2010 | Takagi et al. |
| 2012/0288902 A1 | 11/2012 | Nonaka |

FOREIGN PATENT DOCUMENTS

| | | |
|---|---|---|
| CA | 2386539 | 4/2002 |
| EP | 0620853 B1 | 3/1996 |
| EP | 0931833 A2 | 7/1999 |
| EP | 1234874 A1 | 8/2002 |
| EP | 1389427 A1 | 2/2004 |
| EP | 1571223 A2 | 9/2005 |
| EP | 2133429 A1 | 12/2009 |
| EP | 2138585 A1 | 12/2009 |
| EP | 2246420 A1 | 11/2010 |
| EP | 1769080 B1 | 9/2013 |
| WO | 2004113373 A1 | 12/2004 |
| WO | 2006088231 A1 | 8/2006 |
| WO | 2011065469 A1 | 6/2011 |

OTHER PUBLICATIONS

N. M. Kredich, editors: F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger, "Biosynthesis of Cysteine", *Escherichia coli* and *Salmonella*: cellular and molecular biology, 1996, pp. 514-527, 2nd edition, ASM Press, Washington, D.C.
M. K. Gaitonde, A Spectrophotometric Method for the Direct Determination of Cysteine in the Presence of Other Naturally Occuring Amino Acids, Biochem J. 1967, pp. 627-633, vol. 104.
S.-H. Lee et al., Cysteine produced from lymph node stromal cells suppresses apoptosis of mouse malignant t-lymphoma cells, Biochemical and Biophysical Research Communications, 1995, pp. 837-844, vol. 213, No. 3, Academic Press, Inc.
T. Dassler et al., Identification of a major facilitator protein from *Escherichia coli* involved in efflux of metabolites of the cysteine pathway, Molecular Microbiology, 2000, pp. 1101-1112, vol. 36, No. 5, Blackwell Science Ltd.
International Search Report for PCT/EP2012/062236 dated Sep. 7, 2012.

*Primary Examiner* — Anand Desai
(74) *Attorney, Agent, or Firm* — Caesar, Rivise, Bernstein, Cohen & Pokotilow, Ltd.

(57) ABSTRACT

A method for the production of natural L-cysteine by fermentation in a production fermenter in which a microorganism strain is cultured in a fermentation medium, characterized in that the fraction of the compounds L-cysteine, L-cystine and thiazolidine in the fermentation medium is controlled in a targeted manner by an iron concentration of a maximum of 8 mg/l in the fermentation medium.

12 Claims, No Drawings

METHOD FOR PRODUCTION OF NATURAL L-CYSTEINE BY FERMENTATION

BACKGROUND OF THE INVENTION

The invention relates to a method for the production of natural L-cysteine by fermentation.

The amino acid L-cysteine is used for example as a food additive (particularly in the baking industry), as a feed stock in cosmetics, and also as a starting material for producing pharmaceutical active ingredients (in particular N-acetylcysteine and S-carboxymethylcysteine) and is therefore of economic importance.

L-Cysteine plays a key role in sulfur metabolism in all organisms and is used in the synthesis of proteins, glutathione, biotin, lipoic acid, methionine and other sulfur-containing metabolites. Moreover, L-cysteine serves as a precursor for the biosynthesis of coenzyme A. The biosynthesis of L-cysteine has been investigated in depth in bacteria, particularly in Enterobacteria, and is described in detail in Kredich (1996, Biosynthesis of cysteine, p. 514-527. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology, 2nd ed. ASM Press, Washington, D.C.).

Besides the classical production of L-cysteine by means of extraction from keratin-containing material such as hair, bristles, horns, hooves and feathers or by means of biotransformation by enzymatic conversion of precursors, a method for producing L-cysteine by fermentation was also developed some years ago. The prior art with respect to the production of L-cysteine by fermentation using microorganisms is described in detail e.g. in U.S. Pat. No. 6,218,168B1, U.S. Pat. No. 5,972,663A, US2004038352A2, CA2386539A2, EP1769080 and EP2138585. The bacterial host organisms used here are inter alia strains of the genus *Corynebacterium* and representatives from the family of the Enterobacteriaceae, such as e.g. *Escherichia coli* or *Pantoea ananatis*.

Besides the classic procedure for arriving at improved L-cysteine producers by mutation and selection, targeted genetic modifications to the strains have also been performed in order to achieve an effective L-cysteine overproduction.

For example, the insertion of a cysE allele coding for a serine O-acetyl transferase with a reduced feedback inhibition by L-cysteine led to an increase in cysteine production (U.S. Pat. No. 6,218,168B1). As a result of a feedback-resistant CysE enzyme, the formation of O-acetyl-L-serine, the direct precursor of L-cysteine, is largely decoupled from the L-cysteine level in the cell.

O-Acetyl-L-serine is formed from L-serine and acetyl-CoA. Consequently, the provision of L-serine in a sufficient amount for L-cysteine production is of great importance. This can be achieved by introducing a serA allele coding for a 3-phosphoglycerate dehydrogenase with a reduced feedback inhibition by L-serine. As a result, the formation of 3-hydroxypyruvate, a precursor of L-serine, is largely decoupled from the L-serine level in the cell. Examples of such SerA enzymes are described in EP0620853, U.S. Pat. No. 7,582,460B2 and EP0931833.

Moreover, it is known that the L-cysteine yield in the fermentation can be increased by weakening or destroying genes coding for L-cysteine-degrading enzymes, such as e.g. the tryptophanase TnaA or the cystathionine-β-lyases MalY or MetC (EP1571223).

The increase in the transport of L-cysteine from the cell is a further way of increasing the product yield in the medium. This can be achieved by overexpression of so-called efflux genes. These genes code for membrane-bound proteins which mediate the export of L-cysteine from the cell. Various efflux genes for the L-cysteine export have been described (U.S. Pat. No. 5,972,663A, US2004038352A2, US2005221453, WO2004113373).

The export of L-cysteine from the cell into the culture medium has the following advantages:

1) L-Cysteine is continuously removed from the intracellular reaction equilibrium, with the result that the level of this amino acid in the cell is kept low and consequently the feedback inhibition of sensitive enzymes by L-cysteine does not occur:

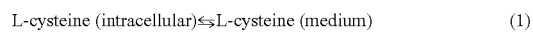

L-cysteine (intracellular)⇌L-cysteine (medium) (1)

2) The L-cysteine released into the medium is oxidized to the disulfide L-cystine in the presence of oxygen, which is introduced into the medium during the culturing (U.S. Pat. No. 5,972,663A):

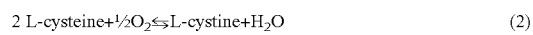

2 L-cysteine+½O₂⇌L-cystine+H₂O (2)

Since the solubility of L-cystine in aqueous solution at a neutral pH is only very low, especially compared to L-cysteine, the disulfide precipitates out even at a low concentration and forms a white precipitate:

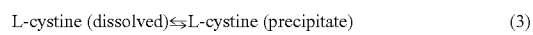

L-cystine (dissolved)⇌L-cystine (precipitate) (3)

By virtue of the precipitation of L-cystine, the level of the product dissolved in the medium is reduced, as a result of which the reaction equilibrium of (1) and (2) in each case is also drawn to the product side.

3) The technical complexity for purifying the product is considerably lower if the amino acid can be obtained directly from the culture medium than if the product accumulates intracellularly and a cell disruption has to be performed first.

During the oxidation of two molecules of L-cysteine, the disulfide L-cystine is formed. This reaction is reversible, which means that L-cystine can be converted back to L-cysteine by reduction. If, after being separated off from the cells (e.g. using a decanter), L-cystine is reduced to L-cysteine again by means of electrolysis, then this chemical conversion means that such L-cysteine cannot be declared as natural according to the flavorings regulation. According to the EU flavorings regulation (1334/2008 Article 22 of the regulation for reforming the labeling regulations under the Foodstuff Law), natural flavorings are defined as follows: "natural" flavorings are chemically defined substances with flavoring properties which occur naturally and have been found in nature. They are obtained by suitable physical, enzymatic or microbiological processes from plant, animal or microbiological starting materials, which are used as such or processed for human consumption by means of one or more conventional food preparation processes (including microbiological processes such as fermentation, see Annex II).

The term "natural" is also used in this sense in the present application. There is great interest in the use of natural raw materials in the manufacture of flavorings. However, there has hitherto been no process for producing natural cysteine by fermentation.

There is a series of compounds which are able to catalyze the oxidation of SH groups; for example, it is known that heavy metal salts such as iron salts or zinc salts are essential additives in fermentations and that these components are able to effectively catalyze the oxidation of cysteine to cystine (US2008190854A2).

U.S. Pat. No. 6,218,168B1 describes that the fermentation medium for the production of L-cysteine and its derivatives comprises an iron concentration of 15 mg/l (75 mg/l iron sulfate heptahydrate). EP1389427A1 discloses a medium for the production by fermentation of L-cysteine, L-cystine and thiazolidine, in which the iron concentration is given as 14.9 mg/l (74 mg/l iron sulfate heptahydrate).

US2010/0093045A1 describes a medium for the production of L-cysteine which comprises only 2 mg/l iron (10 mg/l iron sulfate heptahydrate). However, this medium is used only for use in shake flasks on a laboratory scale (media volume 20 ml) and not for fermentation in a production fermenter. EP2133429A1 mentions a culture medium for the production of L-cysteine, L-cystine, its derivatives or a mixture thereof which comprises only 0.34 mg/l iron (1.7 mg/l iron sulfate heptahydrate). This medium is also not described for a use in fermentation, but for culturing in small tubes (media volume 2 ml). Usually, under these culturing conditions (batch culture, poor oxygen supply, no pH regulation) only very low cell densities (ca. 0.5 to 2 g/l dry biomass) and small product yields are achieved. This is evident by reference to the L-cysteine yields achieved in shake flasks or small tubes of 0.25 g/l (US2003/0077766A1), 0.3 g/l (EP2133429A1) and 1.2 g/l (US2010/0093045A1).

In production fermenters, however, high cell densities are desired in order, as a consequence of the biomass-specific product formation rates, to achieve correspondingly high volumetric yields which only permit an economical process on an industrial scale. The quality of an industrial process for microbiological material production is generally assessed by reference to the productivity. This parameter describes the total amount of product formed per liter of medium per fermentation time.

One disadvantage of the described methods for the production of L-cysteine by fermentation is that the amino acid is present in the culture broth in various forms. In addition to the precipitated L-cystine in the precipitate, soluble L-cysteine, but also L-cystine in dissolved form and thiazolidine are found in the culture supernatant (U.S. Pat. No. 6,218,168B1, U.S. Pat. No. 5,972,663A, CA2386539A2). This thiazolidine (2-methylthiazolidine-2,4-dicarboxylic acid) is the condensation product of L-cysteine and pyruvate, which is formed in a purely chemical reaction.

Within the context of this invention, the term "total cysteine" includes L-cysteine and the L-cystine and thiazolidine compounds derived therefrom and which are formed during the fermentation and accumulate in the culture supernatant and in the precipitate.

In the known methods, the composition of the total cysteine varies at the end of the fermentation: the fraction of precipitated L-cystine is between 40-66% (U.S. Pat. No. 5,972,663A, CA2386539A2), the remaining 34-60% are present in the culture supernatant in the form of soluble products predominantly as L-cysteine and thiazolidine. This product heterogeneity hinders the recovery and purification of the target product natural L-cysteine from the culture broth.

A method would therefore be desirable in which the end product produced is predominantly soluble L-cysteine. Moreover, as far as possible no thiazolidine should be formed. The purification of the target product L-cysteine from the culture supernatant would be considerably easier with such a process since the L-cystine present as precipitate can be separated off together with the cells by a simple separator step, and the soluble L-cysteine can be isolated by ion exchange adsorption.

DESCRIPTION OF THE INVENTION

It is an object of the present invention to provide a method for producing natural L-cysteine in a production fermenter, in which a microorganism strain is cultured in a fermentation medium, where the end product is present predominantly in the form of soluble L-cysteine in the culture medium.

The object is achieved by a method which is characterized in that the fraction of prepared compounds L-cysteine, L-cystine and thiazolidine in the fermenter culture is controlled in a targeted manner by an iron concentration of a maximum of 8 mg/l in the medium.

The iron concentration in the fermentation medium is preferably at a maximum of 4 mg/l, particularly preferably at a maximum of 2 mg/l, iron. It has been found that at these low iron concentrations a significantly more homogeneous product spectrum is present in the fermenter culture since predominantly soluble L-cysteine and precipitated L-cystine, but no thiazolidine, are formed as products. The iron concentration should not fall below 0.2 mg/l, however, since this has an adverse effect on the amount and the fraction of L-cysteine present at the end of the fermentation.

A surprising finding was that in a medium with these low iron concentrations the L-cysteine fraction of the total cysteine can be increased and at the end of the fermentation is at least 65%. This finding is particularly surprising since fermentation media that are described for producing amino acids, specifically L-cysteine and its derivatives, with Enterobacteria contain at least 14.9 mg/l iron (U.S. Pat. No. 6,218,168B1).

It is a further advantage of the present invention that, in contrast to known methods (EP1389427), in the method according to the invention it is not necessary to add reducing agents such as vitamin C, vitamin E or formic acid and salts thereof to stabilize L-cysteine during the process.

The cysteine formation phase of the fermentation method according to the invention starts from the time point at which L-cysteine can be detected in the culture broth for the first time and continues until the end of the cultivation. Typically, this phase starts 2 hours after inoculation of the production fermenter.

In contrast to processes described in the prior art (US2003/0077766A1, EP2133429A1, US2010/0093045A1), with the fermentation method according to the invention cell densities of at least 20 g/l, preferably of at least 30 g/l, particularly preferably of at least 40 g/l dry biomass and volumetric product yields of at least 10 g/l cysteine are achieved.

Microorganisms which can be used for the method according to the invention are all cysteine-producing strains described in the prior art. Such strains are disclosed for example in U.S. Pat. No. 6,218,168B1, U.S. Pat. No. 5,972,663A, US2004038352A2, CA2386539A2, US2009053778A2 and EP2138585A1.

As microorganism strain, preference is given to representatives from the Enterobacteriaceae family, particularly preferably representatives of the genera *Escherichia* or *Pantoea*, very particular preference being given to strains of the species *E. coli* or *P. ananatis*.

Among these microorganism strains, preference is in turn given to strains which either have a modified serine O-acetyl transferase which, compared to the corresponding wild type enzyme, has a feedback inhibition by L-cysteine reduced by at least a factor of 2, or which has, as a result of overexpression of an efflux gene, a cysteine export from the cell that is increased by at least a factor of 2 compared to a wild type cell. Particularly preferred microorganism strains are those which both have a serine O-acetyl transferase which, compared to the corresponding wild type enzyme, has a feedback inhibition by L-cysteine reduced by at least a factor of 2, and also have, as a result of overexpression of an efflux gene, a cysteine export from the cell that is increased by at least a factor of 2 compared to a wild type cell. Such strains are known for example from U.S. Pat. No. 6,218,168B1 and U.S. Pat. No. 5,972,663A. Very particularly preferred strains are those which additionally have a modified 3-phosphoglycerate dehydrogenase with a feedback inhibition by L-serine reduced by at least a factor of 2 compared to the corresponding wild type enzyme (U.S. Pat. No. 7,582,460B2), and in which at least one L-cysteine-degrading enzyme has been attenuated such that only a maximum of 50% of this enzyme activity is still present in the cell compared to a wild type cell.

Preferred variants of the serine O-acetyl transferase have a feedback inhibition by L-cysteine reduced by at least a factor of 5, particularly preferably by at least a factor of 10, very particularly preferably by at least a factor of 50, compared to the corresponding wild type enzyme.

The efflux gene preferably originates from the group ydeD (U.S. Pat. No. 5,972,663A), yfiK (US2004038352 A2), cydDC (WO2004113373), bcr (US2005221453) and emrAB (US2005221453) from *E. coli* or the correspondingly homologous gene from a different microorganism. A homologous gene is to be understood as meaning that the sequence of this gene is in agreement to an extent of at least 80% with the DNA sequence of the corresponding *E. coli* gene.

Compared to a wild type cell, the overexpression of an efflux gene preferably leads to a cysteine export from the cell that is increased by at least a factor of 5, particularly preferably by at least a factor of 10, particularly preferably by at least a factor of 20.

Preferred variants of the 3-phosphoglycerate dehydrogenase have a feedback inhibition by L-serine reduced by at least a factor of 5, particularly preferably by at least a factor of 10, very particularly preferably by at least a factor of 50, compared to the corresponding wild type enzyme.

The L-cysteine-degrading enzyme preferably originates from the group tryptophanase (TnaA) and cystathionine-β-lyase (MalY, MetC).

Particular preference is given to those strains in which at least one of these enzymes has been attenuated such that only at most 10% of the enzyme activity is still present in the cell compared to a wild type strain. Very particular preference is given to strains in which at least one of these enzymes is completely inactivated.

Within the context of the present invention, a production fermenter is preferably to be understood as meaning a fermenter with a nominal volume$\geq 1$ m$^3$. Particular preference is given to using a fermenter with a nominal volume$\geq 5$ m$^3$, very particularly preferably with a nominal volume$\geq 50$ m$^3$.

The cultivation of the cells during the L-cysteine production is carried out under aerobic growth conditions, i.e. in the presence of oxygen. The oxygen content during the production phase of the L-cysteine fermentation should be 30 to 1% O$_2$ saturation, preferably 10 to 1%, particularly preferably 5 to 1%.

The carbon source is preferably sugars, sugar alcohols, organic acids or sugar-containing plant hydrolyzates. Particular preference is given to using glucose, fructose, lactose, glycerol or mixtures comprising two or more of these compounds as carbon source in the method according to the invention.

Preferably, the carbon source is metered in to the culture such that the content of the carbon source in the fermenter during the cysteine production phase does not exceed 10 g/l. Preference is given to a maximum concentration of 2 g/l, particularly preferably of 0.5 g/l, very particularly preferably of 0.1 g/l.

The N source used in the method according to the invention is preferably ammonia, ammonium salts or protein hydrolyzates. When using ammonia as correction means for pH stabilization, this N source is regularly replenished during the fermentation.

As further media additions, salts of the elements phosphorus, chlorine, sodium, magnesium, nitrogen, potassium, calcium, iron and, in traces (i.e. in µM concentrations), salts of the elements molybdenum, boron, cobalt, manganese, zinc and nickel can be added. According to the invention, it is important that for the L-cysteine fermentation the iron concentration of the medium is less than 8 mg/l, preferably less than 4 mg/l, particularly preferably less than 2 mg/l. The iron concentration should not drop below 0.2 mg/l.

Furthermore, organic acids (e.g. acetate, citrate), amino acids (e.g. isoleucine) and vitamins (e.g. B1, B6) can be added to the medium.

Complex nutrient sources that may be used are e.g. yeast extract, corn steep water, soya flour or malt extract.

The incubation temperature for mesophilic microorganisms such as e.g. *E. coli* or *P. ananatis* is preferably 15-45° C., particularly preferably 30-37° C.

The pH of the fermentation medium during the fermentation is preferably in the pH range from 5.0 to 8.5, particular preference being given to a pH of 7.0.

For the preparation of L-cysteine and L-cysteine derivatives, it is necessary to add a sulfur source during the fermentation. In this connection, sulfates or thiosulfates are preferably used. For the L-cysteine fermentation, the thiosulfate concentration of the medium should be below 5 g/l, preferably below 3 g/l, particularly preferably below 1 g/l, very particularly preferably below 0.5 g/l, but should not fall below 0.1 g/l.

Microorganisms which are fermented by the described method secrete L-cysteine and compounds derived therefrom into the culture medium with high efficiency, in a batch or fed batch process following an initial growth phase, over a period of 2 to 30 hours.

To further purify the target product, the following steps can be carried out:
separation step for removing the cells and the L-cystine present as precipitate
isolation of the L-cysteine by ion exchange adsorption
precipitation crystallization
Processes of this type are known from the prior art.

The examples below serve to further illustrate the invention.

EXAMPLE 1

Production of Cysteine Production Strains

The wild type strains *E. coli* W3110 (ATCC 27325) and *P. ananatis* (ATCC 11530) were transformed in each case with the plasmid pACYC184/cysEX-GAPDH-ORF306 (disclosed in example 2 of U.S. Pat. No. 5,972,663A) by means of electroporation as described in U.S. Pat. No. 5,972,663A. The plasmid pACYC184/cysEX-GAPDH-ORF306 contains, besides the replication origin and a tetracycline resistance gene, also the cysEX allele, which codes for a serine O-acetyl transferase with a reduced feedback inhibition by L-cysteine, and the efflux gene ydeD (ORF306), the expression of which is controlled by the constitutive GAPDH promoter.

The selection on plasmid-bearing cells was carried out on LB agar plates containing 15 mg/l tetracycline.

After a further plasmid isolation using the QIAprep Spin Plasmid Kit (Qiagen GmbH) and a restriction analysis, the desired transformants, i.e. cells which have taken up the plasmid pACYC184/cysEX-GAPDH-ORF306, were isolated and used in the fermentation, as described in example 2.

EXAMPLE 2

Culturing of the Cysteine Production Strains with a Differing Supply of Iron Sulfate Heptahydrate To demonstrate the cysteine production, the microorganisms described in example 1 were cultured in fermenters in the fed batch mode with continuous glucose and thiosulfate feed. The production fermenters used were bioreactors with a nominal volume of 5 m$^3$. The inoculation material for the production fermenter was prepared in a two-stage preculture procedure.

Preculture 1 (Shake Flask):
In each case 400 ml of LB medium with 15 mg/l tetracycline were inoculated in ten Erlenmeyer flasks (2000 ml) with the particular strain (*E. coli* W3110 pACYC184/cysEX-GAPDH-ORF306 or *P. ananatis* pACYC184/cysEX-GAPDH-ORF306) and incubated for seven hours on a shaker (150 rpm, 30° C.).

Preculture 2 (Prefermenter):
The preculture 1 from ten Erlenmeyer flasks was then combined. 4 l of preculture 1 were transferred to a sterile inoculation flask and pumped in their entirety into the prefermenter with a nominal volume of 500 l. The fermentation medium (200 l) contained 20 g/l glucose, 10 g/l trypton (Difco), 5 g/l yeast extract (Difco), 5 g/l $(NH_4)_2SO_4$, 1.5 g/l $KH_2PO_4$, 0.5 g/l NaCl, 0.3 g/l $MgSO_4 \times 7\ H_2O$, 0.015 g/l $CaCl_2 \times 2H_2O$, 0.002 g/l $FeSO_4 \times 7\ H_2O$, 1 g/l $Na_3$ citrate$\times$ $2H_2O$, 0.005 g/l vitamin B1, 1 ml/l trace element solution (consisting of 0.15 g/l $Na_2MoO_4 \times 2H_2O$, 2.5 g/l $H_3BO_3$, 0.7 g/l $CoCl_2 \times 6\ H_2O$, 0.25 g/l $CuSO_4 \times 5H_2O$, 1.6 g/l $MnCl_2 \times 4\ H_2O$, 0.3 g/l $ZnSO_4 \times 7\ H_2O$) and 15 mg/l tetracycline.

The pH in the prefermenter was adjusted to 7.0 prior to the inoculation with a 25% $NH_4OH$ solution. During the fermentation, the pH was maintained at 7.0 by automatic correction with 25% $NH_4OH$. The cultures were stirred at 200 rpm and at the start gassed with 0.5 vvm of a compressed air sterilized via a sterile filter. The oxygen probe had been calibrated to 100% saturation under these starting conditions before the inoculation. The desired value for the $O_2$ saturation during the fermentation was set at 30±1%. After the $O_2$ saturation dropped below the desired value, a regulation cascade was started in order to restore the $O_2$ saturation to the desired value. Here, the gas introduction was increased continuously to a maximum of 2 vvm.

The cultivation was carried out at a temperature of 30° C. and a pressure of 50 kPa for 15 h. After this incubation, the optical density at 600 nm ($OD_{600}$) was between 18 and 20.

Main Culture (Production Fermenter):
The fermentation was carried out in fermenters with a nominal volume of 5 m$^3$. The fermentation medium (2300 l) comprises 15 g/l glucose, 10 g/l trypton (Difco), 5 g/l yeast extract (Difco), 5 g/l $(NH_4)_2SO_4$, 1.5 g/l $KH_2PO_4$, 0.5 g/l NaCl, 0.3 g/l $MgSO_4 \times 7\ H_2O$, 0.015 g/l $CaCl_2 \times 2\ H_2O$, 1 g/l $Na_3$ citrate$\times 2H_2O$ and 1 ml trace element solution (see above), 0.005 g/l vitamin B1 and 15 mg/l tetracycline. Depending on the experimental mixture, the medium was supplemented with 75 mg/l, 40 mg/l, 20 mg/l, 10 mg/l, 3 mg/l or 0.5 mg/l $FeSO_4 \times 7\ H_2O$. The pH in the production fermenter was adjusted to 7.0 prior to the inoculation by pumping in a 25% $NH_4OH$ solution. During the fermentation, the pH was maintained at a value of 7.0 by automatic correction using 25% $NH_4OH$. For the inoculation, 200 l of preculture 2 were pumped into the fermenter vessel. The starting volume was thus about 2500 l. The cultures were stirred at the start at 120 rpm and gassed with 1.5 vvm of compressed air sterilized via a sterile filter. The oxygen probe had been calibrated to 100% saturation prior to the inoculation under these starting conditions. The desired value for the $O_2$ saturation during the fermentation was adjusted to 30±1%. After the $O_2$ saturation dropped below the desired value, a regulation cascade was started in order to restore the $O_2$ saturation to the desired value. Here, firstly the gas introduction was continuously increased (to max. 2 vvm) and then the stirring speed was continuously increased (to max. 300 rpm).

The fermentation was carried out at a temperature of 30° C. and a pressure of 50-60 kPa. After a fermentation time of 2 h, the continuous feeding in of a sulfur source in the form of a sterile 60% sodium thiosulfate$\times 5H_2O$ stock solution was carried out. The feed rate was adjusted such that the thiosulfate concentration in the medium never exceeded 5 g/l. As soon as the glucose content in the fermenter had dropped from an initial 15 g/l to ca. 2 g/l, a 56% glucose solution was continuously metered in. The feed rate was adjusted such that the glucose concentration in the fermenter from that point on did not exceed 10 g/l. The glucose determination was carried out using a glucose analyzer from YSI (Yellow Springs, Ohio, USA).

The fermentation time was 24 hours. Then, cell densities of 40 to 45 g/l dry biomass were determined in all fermenters. At the end of the fermentation, samples were taken and the content of L-cysteine and the derivatives derived therefrom in the culture supernatant (L-cystine and thiazolidine) and in the precipitate (L-cystine) were each determined separately from one another (see tables 1 and 2). For this purpose, the colorimetric ninhydrin test from Gaitonde was used in principle (Gaitonde, M. K. (1967), Biochem. J. 104, 627-633). Here, it is to be ensured that, under the strongly acidic reaction conditions of the test, not only is free L-cysteine included and quantified, but also the L-cysteine bonded in the thiazolidine. L-Cystine dissolved in the culture supernatant is detected in the ninhydrin test from Gaitonde likewise as L-cysteine following reduction with dithiothreitol (DTT) in dilute solution at pH 8.0. The L-cystine in the precipitate had to first be dissolved in 8% hydrochloric acid before it could be quantified in the same way.

For the differential quantification of the components L-cysteine, L-cystine and thiazolidine dissolved in the culture supernatant, two further test methods were additionally used: the quantification of free L-cysteine was carried out by the test described by Sang-Han Lee et al. (1995, Biochemical and Biophysical Research Communications 213, 837ff) by means of 5,5'-dithiobis-2-nitrobenzoic acid (DTNB), with which free SH groups can be specifically detected. The differentiation of L-cysteine and the derivatives L-cystine and thiazolidine was carried out by means of an HPLC method, as described in Daβler et al. (2000, Molecular Microbiology 36, 1101ff).

TABLE 1

Content of L-cysteine and L-cysteine derivatives in the culture broth of E. coli after 24 h as a function of the iron concentration in the medium

| | | E. coli | | | | |
|---|---|---|---|---|---|---|
| | | Cysteine content after 24 h [g/l] | | | | Fraction of |
| FeSO$_4$ | | Supernatant | | | | L- |
| x7H$_2$O [mg/l] | Fe [mg/l] | L-Cysteine[1] | L-Cystine[2] | Thiazo lidine[3] | Precipit ate[4] | cysteine [%][5] |
| 75 | 15 | 8.8 | 1.2 | 1.2 | 11.6 | 38.6 |
| 40 | 8 | 14.6 | 1.2 | 0.2 | 6.4 | 65.2 |
| 20 | 4 | 17.6 | 1.0 | 0 | 5.8 | 72.1 |
| 10 | 2 | 19.6 | 1.0 | 0 | 4.0 | 79.7 |
| 3 | 0.6 | 19.8 | 0.8 | 0 | 4.4 | 79.2 |
| 0.5 | 0.1 | 7.2 | 0.8 | 0 | 9.4 | 41.4 |

[1]L-Cysteine in the supernatant (DTNB test)
[2]Dissolved L-cystine in the supernatant (HPLC)
[3]Thiazolidine in the supernatant (HPLC)
[4]L-Cystine in the precipitate
[5]Fraction of L-cysteine in the total cysteine

TABLE 2

Content of L-cysteine and L-cysteine derivatives in the culture broth of P. ananatis after 24 h as a function of the iron concentration in the medium

| | | P. ananatis | | | | |
|---|---|---|---|---|---|---|
| | | Cysteine content after 24 h [g/l] | | | | Fraction |
| | | Supernatant | | | | of |
| FeSO$_4$ x7H$_2$O [mg/l] | Fe [mg/l] | L-Cysteine[1] | L-Cyst-ine[2] | Thiazol idine[3] | Precipi tate[4] | L-cysteine [%][5] |
| 75 | 15 | 5.8 | 1.4 | 1.2 | 7.6 | 36.3 |
| 40 | 8 | 10.4 | 1.2 | 0.2 | 4.8 | 62.7 |
| 20 | 4 | 12.6 | 1.2 | 0 | 4.4 | 69.2 |
| 10 | 2 | 14.6 | 1.0 | 0 | 3.8 | 75.3 |
| 3 | 0.6 | 14.8 | 1.0 | 0 | 4.0 | 74.7 |
| 0.5 | 0.1 | 5.2 | 0.8 | 0 | 7.6 | 38.2 |

[1]L-Cysteine in the supernatant (DTNB test)
[2]Dissolved L-cystine in the supernatant (HPLC)
[3]Thiazolidine in the supernatant (HPLC)
[4]L-Cystine in the precipitate
[5]Proportion of L-cysteine in the total cysteine

The invention claimed is:

1. A method for the targeted control of fractions of L-cysteine, L-cystine and thiazolidine in a total cysteine in a fermentation medium during a preparation by fermentation of natural L-cysteine in a production fermenter with a nominal volume ≥1 m$^3$, said method comprising culturing a microorganism strain from the Enterobacteriaece family in the fermentation medium, wherein the microorganism strain both has a modified serine O-acetyl transferase which, compared to a corresponding wild type enzyme, has a feedback inhibition by L-cysteine reduced by at least a factor of 2, and also has, as a result of overexpression of an efflux gene, a cysteine export from a cell that is increased by at least a factor of 2 compared to a wild type cell, wherein the iron concentration is at a maximum of 8 mg/l and a minimum of 0.6 mg/l and is achieved by increasing the L-cysteine fraction of the total cysteine to at least 65% in the fermentation medium.

2. The method as claimed in claim 1, wherein the iron concentration in the fermentation medium is at a maximum of 4 mg/l iron.

3. The method as claimed in claim 1, wherein no reducing agents are added.

4. The method as claimed in claim 1, wherein the microorganism strain used is a representative of the genera Escherichia or Pantoea.

5. The method as claimed in claim 1, wherein the microorganism strain additionally has a modified 3-phosphoglycerate dehydrogenase with a feedback inhibition by L-serine reduced by at least a factor of 2 compared to the corresponding wild type enzyme, and in which at least one L-cysteine-degrading enzyme has been attenuated such that only a maximum of 50% of this enzyme activity is still present in the cell compared to a wild type cell.

6. The method as claimed in claim 1, wherein the culturing of the cells is carried out in a fermenter with a nominal volume ≥5 m$^3$.

7. The method as claimed in claim 1, wherein a thiosulfate concentration in the fermentation medium is 0.1 g/l to less than 5 g/l.

8. The method as claimed in claim 2, wherein no reducing agents are added.

9. The method as claimed in claim 8, wherein the microorganism strain used is a representative of the genera Escherichia or Pantoea.

10. The method as claimed in claim 9, wherein the microorganism strain additionally has a modified 3-phosphoglycerate dehydrogenase with a feedback inhibition by L-serine reduced by at least a factor of 2 compared to the corresponding wild type enzyme, and in which at least one L-cysteine-degrading enzyme has been attenuated such that only a maximum of 50% of this enzyme activity is still present in the cell compared to a wild type cell.

11. The method as claimed in claim 10, wherein the culturing of the cells is carried out in a fermenter with a nominal volume ≥5 m$^3$.

12. The method as claimed in claim 1, wherein a thiosulfate concentration in the fermentation medium is 0.1 g/l to less than 5 g/l.

* * * * *